(12) United States Patent
Saito et al.

(10) Patent No.: US 7,067,496 B2
(45) Date of Patent: Jun. 27, 2006

(54) METHODS FOR INTRODUCING GENES INTO MAMMALIAN SUBJECTS

(75) Inventors: Norimitsu Saito, Kanagawa (JP); Ming Zhao, San Diego, CA (US)

(73) Assignee: AntiCancer, Inc., San Diego, CA (US)

( * ) Notice: Subject to any disclaimer, the term of this patent is extended or adjusted under 35 U.S.C. 154(b) by 942 days.

(21) Appl. No.: 09/734,786

(22) Filed: Dec. 11, 2000

(65) Prior Publication Data

US 2002/0012661 A1 Jan. 31, 2002

Related U.S. Application Data

(60) Provisional application No. 60/170,166, filed on Dec. 10, 1999.

(51) Int. Cl.
*A61K 31/7088* (2006.01)
*C12N 15/63* (2006.01)
*C12N 5/06* (2006.01)

(52) U.S. Cl. .................... 514/44; 435/455; 435/347; 435/381

(58) Field of Classification Search ............... 514/44; 435/347, 456, 458
See application file for complete search history.

(56) References Cited

U.S. PATENT DOCUMENTS

| 5,266,480 A | 11/1993 | Naughton et al. .... 435/240.243 |
| 5,641,508 A * | 6/1997 | Li et al. ..................... 424/450 |
| 5,672,508 A | 9/1997 | Beach et al. |

FOREIGN PATENT DOCUMENTS

| DE | 197 40 092 | 3/1999 |
| DE | 197 40 092 A1 * | 3/1999 |
| EP | 0 633 315 | 1/1995 |
| WO | WO 94/22468 | 10/1994 |
| WO | WO 96/25422 | 8/1996 |
| WO | WO 98/22589 | 5/1998 |
| WO | WO 98/46208 | 10/1998 |
| WO | WO 00/05366 | 2/2000 |

OTHER PUBLICATIONS

Verma et al., Gene therapy-promises, problems and prospects, 1997, NATURE, vol 389, pp. 239-242.*
Marshall, Gene therapy's growing pains, 1995, SCIENCE, vol. 269, pp. 1050-1055.*
Orkin et al., Report and recommendations of the panel to assess the NIH investment in research on gene therapy, 1995.*
Poston et al., Ex vivo gene therapy prevents chronic graft vascular disease in cardiac allografts, 1998, The Journal of Thoracic and Cardiovascular Surgery, vol. 116, pp. 386-396.*
Chapelier et al., Gene therapy in lung transplantation: Feasibility of ex vivo adenovirus-mediated gene transfer to the graft, 1996, Human Gene Therapy, vol. 7, pp. 1837-1845.*
Alexeev et al., Nature Biotechnol. (1998) 16:1343-1346.
Choate et al., Nature Med. (1996) 2:1263-1267.
Deng et al., Nature Biotechnol. (1997) 15:1388-1391.
Domashenko et al., J. Invest. Dermatol. (1999) 112:552.
Falo, Proc. Assoc. Am. Physicians (1989) 111:211-219.
Fan et al., Nature Biotechnol. (1999) 17:870-872.
Li et al., Nature Med. (1995) 1:705-706.
Park et al., Experimental & Molecular Medicine (1997) 29(1):65-69.
Reynolds et al., Nature (1999) 402:33-34.
Shi et al., Vaccine (1999) 17:2136-2141.
Tang et al., Nature (1997) 388:729-730.
Tuting et al., J. Invest. Dermatol. (1998) 111:183-188.
Yu et al., J. Invest. Dermatol. (1999) 112:370-375.

* cited by examiner

*Primary Examiner*—Daniel M. Sullivan
(74) *Attorney, Agent, or Firm*—Morrison & Foerster LLP (57) ABSTRACT

Methods to obtain genetic modifications of cells in histoculture are described. Modification is assisted by treating the histoculture with collagenase prior to contacting the histoculture with the delivery vehicle for the desired gene. Hair follicles and other organized tissues can be modified in this was and then transplanted into intact recipients.

14 Claims, 3 Drawing Sheets

METHODS FOR INTRODUCING GENES INTO MAMMALIAN SUBJECTS

CROSS-REFERENCE TO RELATED APPLICATION

This application claims priority under 35 U.S.C. § 119(e) from provisional application Ser. No. 60/170,166, filed Dec. 10, 1999, the contents of which are incorporated herein by reference.

TECHNICAL FIELD

The invention relates to modifying mammalian subjects to contain heterologous genes. More particularly, the invention concerns treating histocultured tissue, including hair follicles, ex vivo and re-implanting tissue or hair follicles into a recipient.

BACKGROUND ART

Somatic modification of the genetic complement of mammalian subjects, including humans, has been attempted using a variety of techniques. For example, adenoviral vectors containing a desired gene can be used directly to infect tissues and organs in situ. More typically, perhaps, cell cultures or suspensions of cells are modified ex vivo and then returned to the intact subject via the bloodstream. For example, an RNA-DNA oligonucleotide (RDO) designed to correct the albino point mutation in the mouse tyrosinase gene was able to correct this condition in cultured albino melanocytes (Alexeed, D., et al., *Nature Biotechnol* (1998) 16:1343–1346). This work was extended to in vivo correction of the same defect by delivering the RDO in liposomes or by intradennal injection as reported by the same group (Alexeed, D., et al., *Nature Biotechnol* (1999) 16:1343–1346. Earlier work had described selective gene therapy of hair follicles using a liposome-entrapped lac Z (Li, L., et al., *Nature Med* (1995) 1:705–706). Preferred recipients of the liposomal compositions were endogenous hair follicles in the anagen phase (Domashenko, A., et al., *J. Invest Dermatol* (1999) 112:552).

Thus, it has been possible to modify hair follicle cells individually in culture and to modify intact hair follicles in vivo. It has also been shown that cultured mutant skin keratinocytes from patients with lamellar ichthyosis can be safely modified genetically in vitro and then transplanted into nude mice to obtain a normal epidermis (Choate, K. A., et al., *Nature Med* (1996) 2:1263–1267.) Similarly, keratinocytes cultured individually in vitro can be modified genetically and then transplanted into nude mice to obtain re-formed tissue (Deng, H., et al., *Nature Biotechnol* (1997) 15:1388–1391). It has also been shown that hair follicles will form from hair follicle dermal sheath cells taken from the scalp of a different individual (Reynolds, J., et al., *Nature* (1999) 402:33–34).

In short, it has been shown that individual cells can be modified genetically and then transplanted to an intact organism and that individual cells, when transplanted can, under appropriate conditions, form an organized tissue.

Direct application of genes or DNA in general to human skin has also been shown to be effective, at least in terms of immunization with respect to an encoded antigen. This has been reported by a number of groups including Tang, D-C, et al., *Nature* (1997) 388:729–730; Yu, W-H, et al., *J. Invest Dermatol* (1999) 112:370–375; Falo, L. D. Jr., *Proc Assoc Am Physicians* (1989) 111:211–219; Shi, Z., et al., *Vaccine* (1999) 17:2136–2141; and Tuting, P., et al., *J. Invest Dermatol* (1998) 111:183–188. Fan, H., et al., *Nature Biotechnol* (1999) 17:870–872 further showed that to elicit a response to a hepatitis B surface antigen, the gene encoding this antigen was effective when applied to normal skin containing hair follicles. However, skin lacking hair follicles was not a suitable target for vaccination.

DISCLOSURE OF THE INVENTION

The invention resides in the discovery that histocultured tissues, including tissues containing hair follicles, can be successfully modified genetically ex vivo and then transplanted successfully into an intact mammalian subject. The success of the modification is enhanced by treating the histocultured tissues with collagenase prior to genetic modification.

Thus, in one aspect, the invention is directed to a method to deliver a nucleic acid to a tissue which method comprises treating a histoculture of said tissue with said nucleic acid, optionally preceded by the step of treating said tissue with collagenase. A preferred tissue is tissue containing hair follicles.

In additional aspects, the invention is directed to methods to introduce a nucleic acid molecule into a mammalian subject which comprises transplanting into the dermis of said subject at least one hair follicle that has been modified ex vivo to contain the nucleic acid molecule, or transplanting into the corresponding tissue of the subject a histocultured tissue that has been modified ex vivo to contain the nucleic acid molecule. In both cases, the histoculture is treated with collagenase prior to the step of modifying with the desired nucleic acid.

In still another aspect, the invention is directed to histocultured tissue modified to contain heterologous nucleic acids.

MODES OF CARRYING OUT THE INVENTION

The use of histocultured tissue as the substrate for genetic modification has several advantages over direct in vivo application and over ex vivo modification of individually cultured cells for subsequent transplant in vivo. The tissue retains its three-dimensional integrity and is thus more readily reconstituted when transplanted into the recipient. By manipulating the tissue ex vivo, the level of genetic modification can be controlled and success measured prior to invasive treatment of the subject. Although it is advantageous to treat the cultured tissue with collagenase in order to enhance the ability of the tissue to accept heterologous nucleic acids, the treatment is not so severe as to destroy completely the integrity of the three-dimensional array.

The three-dimensional histoculture can be assembled from any tissue, including skin, especially skin containing hair follicles, lymphoid tissue, or tumor tissue. The choice of tissue will depend on the nature of the treatment contemplated. The histoculture maintains the organization of the tissue sample which is provided as an intact fragment. By "intact" is meant that the three-dimensional organization of the tissue is preserved in the histoculture both before and after modifying the cells to contain a heterologous nucleic acid. As described below, the histoculture may be treated with collagenase prior to supplying the appropriate nucleic acid-containing vector or formulation containing the nucleic acid. However, the treatment with collagenase must be sufficiently mild to preserve the essential elements of organization. Thus by "intact" tissue, or "intact" fragment is meant the fragment of tissue as obtained from a donor subject both before and after treatment with collagenase according to the method of the invention.

For example, hair follicles are useful recipients of genes intended to affect the growth or quality of hair, but also are able to produce immunogens and other products that may be useful to the organism taken as a whole. Thus, a transformation of hair follicles can readily be used as an intermediate step in genetic therapy directed to the whole organism. Immunization, for example, through modifying the hair follicles to produce the required antigen is consistent with the observation, reported above, that only skin containing hair follicles is able to accept DNA for eliciting an immune response against an antigen, whereas skin devoid of hair follicles is incapable of doing so.

Thus, hair follicles or skin containing hair follicles would be removed from a non-critical area of a subject to be treated and cultured in vitro. Preferably, the skin containing hair follicles would be histocultured. The histocultured skin is then treated with collagenase in an amount and for a time sufficient to enhance the ability of the hair follicles to take up heterologous nucleic acid, but the treatment is regulated so as not to result in disintegration of the histoculture. The intact hair follicles in culture or in histoculture are then treated with a suitable vector to deliver desired nucleic acids. Such vectors include viral vectors such as adenoviral vectors or retroviral vectors or the supernatants from packaging cells.

In general, in one aspect the invention relates to the use of hair follicles as a delivery system for gene expression vectors or for naked DNA. In order to practice the invention, proper methods to harvest and treat the hair follicles should be employed; various means are available to modify the hair follicles; the follicles can then be re-implanted into the recipient.

For harvesting the hair follicles, preferably skin containing the follicles is removed in small pieces from a suitable donor. If the follicles are already in anagen phase, they can directly be histocultured. However, if the donor contains hair follicles that are not in anagen phase, they can be resynchronized by depilating the skin using, for example, a wax procedure, and then removing the hair follicle-containing skin pieces at an appropriate later time when anagen has been established. Typically, this is after 3–10 days, more preferably 5–7 days, and most preferably 6 days in murine subjects; other mammalian subjects will exhibit varying time periods to reestablish anagen. An optimum waiting period can readily be determined. The skin containing hair follicles in anagen phase is then embedded in a three-dimensional matrix, typically collagen based. It has been found by the present inventors that subsequent modification with the desired heterologous gene is improved if the histoculture is then treated with collagenase or other appropriate lytic enzyme to facilitate infection or transduction.

The treatment with collagenase should be sufficient to enhance the subsequent genetic modification, but not so severe as to destroy the integrity of the histoculture. The extent of collagenase digestion can be regulated by controlling the concentration of collagenase, the temperature of incubation, and the time of incubation. These are interdependent factors and optimum levels can readily be determined empirically. Typical suitable conditions are about 2 mg/ml collagenase solution for 1–2 hours at 37° C.

After "loosening" the supporting matrix, the histoculture is in an appropriate condition to accept genetic alteration. The factors to be considered in this step are the nature of the method of modification—i.e. the vector system or methodology used and the nature of the genes to be inserted.

Genetic alteration is typically accomplished by treating with liposomal based systems or lipofection in general, including commercial systems. Viral vectors such as adenoviral vectors and retroviral vectors, and, in the case of viral vectors in general, supernatants from packaging cells for such vectors. Transduction under suitable conditions with naked DNA can also be accomplished.

Figure 1:
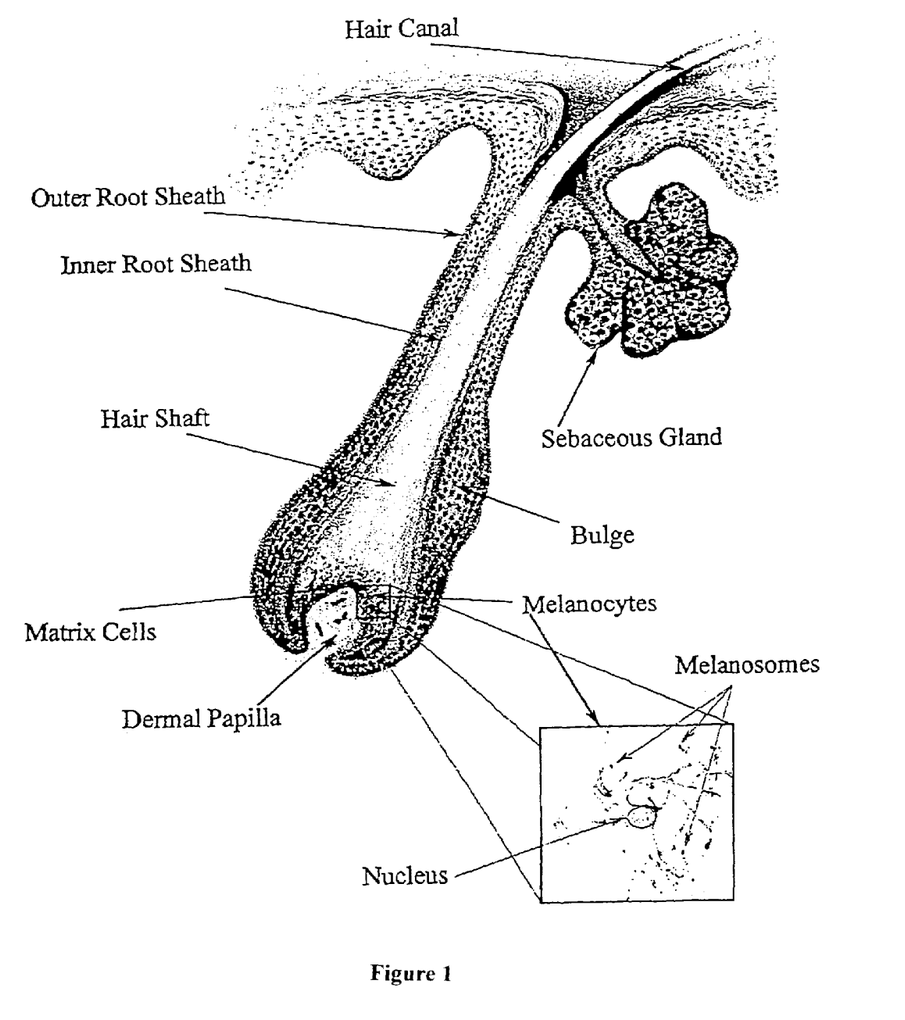
FIG. 1 is a diagram of a typical hair follicle.

FIG. 1 shows a diagram of a typical hair follicle. As seen, the hair canal is coupled to a sebaceous gland which secretes lipids. It has been found by applicants herein that selective delivery of compositions in general to the hair follicle can be accomplished using liposomal compositions. See, for example, U.S. Pat. No. 5,914,126, incorporated herein by reference. Thus, in the histocultured sample, treated optionally with collagenase, selective delivery to the hair follicle of nucleic acids intended for hair follicle-specific effects can be accomplished.

In the alternative method of the invention, especially where generalized local, or systemic delivery of the nucleic acid molecule is desired, a histocultured sample of the dermis or other tissue of the subject can be used. In this instance, selective delivery is not required. Suitable techniques for histoculturing samples generally are well known; those disclosed, for example, in U.S. Pat. No. 5,849,579, and U.S. Pat. No. 5,726,009, incorporated herein by reference are preferred.

The genes to be inserted can be provided operably linked to their own control sequences or naked DNA may be supplied which will co-opt promoters endogenous to the hair follicle cells. The control sequences typically include promoters which may be a constitutive or inducible that are compatible with mammalian cells. Such promoters include, but are not limited to, the CMV promoter, the HSV promoter, the LTR from adenovirus, and the metallothionine promoter.

Suitable nucleotide open reading frames include those encoding proteins which elicit immune responses, regulate hair growth, modify hair color, or which are hormones or therapeutic compounds. The choice of nucleotide sequence will depend on the circumstances and the desired result. Thus, for example, if the end result desired is to supply the recipient with hair having certain characteristics of color and density, nucleotide open reading frames encoding proteins such as tyrosinase which participate in the generation of melanin might be included; also included might be nucleotide sequences encoding proteins that stimulate hair growth. The suitable method in this case would include implantation of hair follicles which had been modified according to the method of the invention into the dermis of the recipient. If the purpose is to effect immunization of an individual with regard to a pathogen such as a protozoan, a bacterium, or a virus, an appropriate immunogen, such as hepatitis B surface antigen, a viral coat protein, a peptide subunit of bacterial or protozoal surface antigen, or other peptide based immunogen would be encoded by the nucleotide sequence. In this instance, either implantation of hair follicles that had been modified according to the method of the invention, or a histocultured tissue sample generally could be employed. As noted above, the histocultured sample could include, in addition to skin, lymphoid tissue or tumor tissue. In addition, it is included within the scope of the invention to modify the metabolism of the subject by, in effect, administering hormones or therapeutic agents such as FSH, LH, human growth hormone, thyroid stimulating hormone, oxytocin, calcitonin, tissue plasminogen activator, erythopoietin, various cytokines such as the interleukins and the like by providing nucleotide sequences that encode them. Both a local and systemic effect will result. Either implantation of modified hair follicles or histocultured sections in general may be used.

As described above, the nucleotide sequences encoding the desired proteins may be provided as naked DNA; however, it is preferable to provide these nucleotide sequences in the form of constructs which provide control sequences for expression. The constructs may further provide the mechanism for transduction of the cells in the hair follicle or tissue sample by infection such as realized with viral vectors or alternative means to transduce the target cells, such as lipofection, use of liposomes, electroporation and the like may also be employed.

When the hair follicles or tissue have been modified to contain the genetic constructs described above, these are then implanted into a suitable recipient. Techniques for implantation of hair follicles and implantation of tissue, including tissue containing hair follicles, into recipient subjects are well known in the art. The hair follicle or tissue which has been histocultured are provided as intact, organized implants.

The subjects that are the recipients of the implants are mammalian subjects. In order to prevent rejection of the implanted tissue, It is preferable that the recipient be syngeneic with the donor of the hair follicle or cultured tissue, or that the recipient be immunocompromised. Implantation of hair follicles in allograft settings in humans is well known. Similarly, in human subjects, the individual's own dermal tissue, for example, is the clearly preferred selection for genetic modification prior to reimplantation into the same subject. If, however, for some reason, the dermis of the same individual cannot be employed, the implantation of tissue from another donor would be, as is conventional, accompanied by administration of immunosuppressants.

Similar considerations apply with regard to veterinary use for administration of nucleic acid constructs which will produce immunogens, hormones or therapeutic compounds.

For use in laboratory context, the implantation techniques are useful in generating modified subjects such that the effect of the proteins introduced by this gene therapy method can be evaluated. In effect, the technique produces a transgenic subject which can then be used as an experimental model to evaluate the effects of administering other substances to the model system. In this context, the tissue modified may be derived from the same or syngeneic subject, or an immunocompromised recipient such as a SCID mouse or nude mouse can be used as a recipient for tissue derived from an arbitrary source. In addition to these murine immunocompromised subjects, other mammals can be immunocompromised by radiation or immunosuppressants as has been described, for example, in horses by Hodgin, E. C., et al., *M.J. Vet. Res.* (1978) 39:1161–1167; Perryman, L. E., et al., *Thymus* (1984) 6:263–272; in dogs, by Roth, J. A. et al., *M.J. Vet. Res.* (1984) 45:1151–1155; and in monkeys by Baskin, G. B., *Am. J. Pathol.* (1987) 129:345–352.

Thus, any mammalian subject is appropriate as a recipient of the transplanted modified organized tissue or hair follicle. Subjects can include, in addition to humans, veterinary subjects such as horses, cows, pigs, sheep, dogs and cats, as well as laboratory animals such as rabbits, mice and rats.

Although it is possible to utilize tissue from arbitrary sources for transplantation into the recipient provided steps are taken to assure a sufficiently immunocompromised state on the part of the recipient, one of the advantages of the present invention is that by using dermal tissue and/or hair follicles as vehicles for delivery of genetic constructs, it is frequently possible to utilize an allograft. This bypasses the complications that might otherwise accompany efforts at immunocompromise.

EXAMPLES

The following examples are intended to illustrate, but not to limit, the invention.

Methods to Assess GFP-transduced Hair Follicles and Shafts

The number of hair follicles and GFP-positive hair follicles was determined under bright-field microscopy and fluorescent-field microscopy. The calculations were based on average number of hairs from 5 randomly chosen microscopic fields covering an area of 0.581 mm$^2$ (1 field of 200× magnification). At least 500 hairs per group were counted to generate the percentage of GFP-positive hair follicles. Hair follicles in which GFP was visualized anywhere in the hair bulb or shaft were scored as GFP positive.

A Nikon (Tokyo, Japan) fluorescent microscope and a Leica fluorescence stereo microscope model LZ12 (Leica Inc., Deerfield, Ill.) equipped with a mercury 50 W lamp power supply were used. Emitted fluorescence was collected through a long-pass filter GG475 (Chroma Technology, Brattleboro, Vt.) on a Hamamatsu C5810 3-chip cooled color CCD camera (Hamamatsu Photonics Systems, Bridgewater, N.J.).

After viral GFP transduction, skin pieces were taken at several time points for histological study to determine the location of GFP expression. Pieces of histocultured skin or skin grafts were incubated in a 2 mg/ml type I collagenase solution in culture medium for 2 hr at 37° C., and rinsed in culture medium in order to release hair follicles. Alternatively, for histological studies, pieces of histocultured skin or skin grafts were stored −80° C. Frozen specimens were sectioned on a cryostat (Hacker Instruments, Inc., Fairfield, N.J.) and collected onto glass slides (Fisher Scientific, Pittsburgh, Pa.).

In addition, RNA was isolated from histocultured or grafted skin subjected to RT-PCR. Skin samples (100 mg) were homogenized in 1 ml of TRI REAGENT (Sigma, St. Louis, Mo.) to extract RNA (13,14). For RT-PCR, approximately 10 μg of RNA was reversely transcribed to first cDNA chains. Reverse transcription was carried out in 20 μl of first-strand buffer, 500 μM of each dNTP, and 20 units of AMV reverse transcriptase (Strategene, San Diego, Calif.). The primer for the first strand was pGFP antisense. Incubation was at 42° C. for 50 min. The products of the reverse transcription were then amplified by the PCR. Mouse β-actin mRNA was used as the standard. As a control, mouse β-actin (514 bp) was amplified by the RT-PCR in extracted RNA from both the GFP-positive and -negative skin. The sequence of the GFP upstream primer was 5'-ATG GCT AGC AAA GGA GAA GAA CT-3' (SEQ ID NO:1). The downstream primer was 5'-TCA GTT GTA CAG TTC ATC ACT G-3' (SEQ ID NO:2). The PCR conditions for both GFP and β-actin were as follows: first denaturation at 97° C. for 30 seconds; annealing at 55° C. for 30 seconds; and extension at 72° C. for 45 seconds; then a final extension at 72° C. for 10 minutes.

Example 1

Genetic Modification of Hair Follicles of Histocultured Skin

C57BL/10 and albino mice were used in this study. The hair follicles when modified were in anagen phase. The hair follicles of six-day-old mice used in the study were naturally in anagen phase. Eight-week-old mice used in the study, judged to be in telogen by their pink color, were anesthetized and treated to place the hair follicles in synchronized anagen by depilation with wax in a 3×5 cm dorsal area; i.e., the hair follicles in eight-week-old mice were natively in telogen phase, but converted to anagen phase six days after depilation from the dorsal area.

In each case, subcutaneous tissue was removed and cut into pieces of 1 mm×2 mm. The skin pieces were histocultured. Some of the histocultured specimens were treated with collagenase by incubating in 2 mg/ml collagenase solution in culture medium (RPMI 1640, 10% FBS) for 1–2 hours at 37° C. The histocultures treated with collagenase were then rinsed in PBS.

In more detail, animals were sacrificed by cervical dislocation on the $6^{th}$ day after depilation. The back skin was dissected at the level of the subcuitis. Subcutaneous tissue was removed and the skin was rinsed in calcium- and magnesium-free phosphate buffered saline (CMF-PBS, pH 7.4). The skin samples were cut into small pieces (1 mm×1 mm~2 cm×2 cm). A fraction of the specimens were directly used as untreated controls cultured in RPMI 1640 containing 10% fetal bovine serum (FBS). The remainder of the specimens were incubated in a 2 mg/ml type I collagenase (Sigma, St. Louis, Mo.) solution in medium from 45 min to 3 hr 45 min at 37° C. and rinsed in CMF-PBS.

Both untreated and treated cultures were incubated at 37° in humidified 5% $CO_2$/95% air and then infected with pQBI-AdCMV5GFP (Quantum, Montreal, Quebec) at $2.4 \times 10^6$ to $5.0 \times 10^9$ plaque forming units (PFU) per ml in the culture medium for 90 minutes then incubated in fresh RPMI 1640 (10% FBS) at 37° for 1–6 hours. The expression of green fluorescent protein (GFP) was then observed over several days. The results are shown in Table 1. It is seen that successful genetic modification is achieved both with and without collagenase but that this is improved by treatment with collagenase.

Figure 2A:
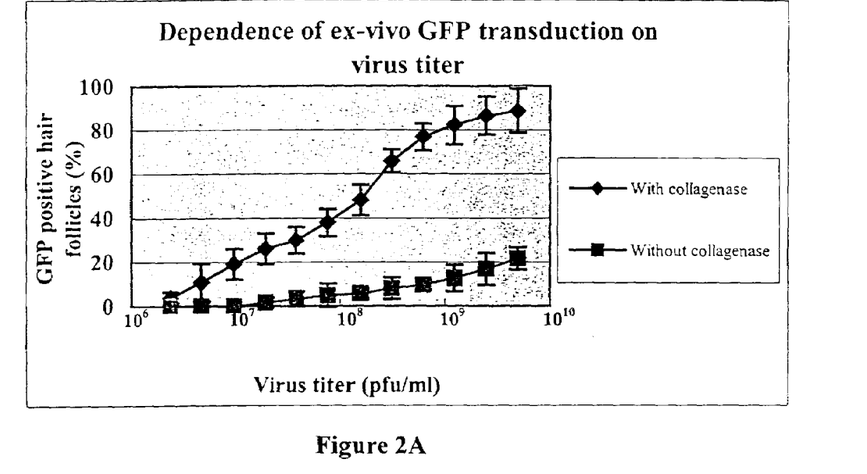
FIGS. 2A and 2B are a graphic representation of adenoviral-delivered GFP in histocultured skin with and without treatment with collagenase, as a function of virus titer and of virus incubation time, respectively.

In similar experiments, both collagenase-treated and untreated skin histocultures were treated with adenoviral GFP at a range of $2.4 \times 10^6$ to $5.0 \times 10^9$ pfu/ml for 2.5 hr at 37° C. On day-3 after GFP transduction, the number of GFP positive hair follicles in collagenase-treated histocultures increased up to 80% with higher virus titer. In untreated histocultures, the number of GFP positive hair follicles was very small and increased only slightly with higher titer and was 4 times less than collagenase-treated histocultures. These results are shown in FIG. 2A, indicating the dependence on virus titer.

Figure 2B:
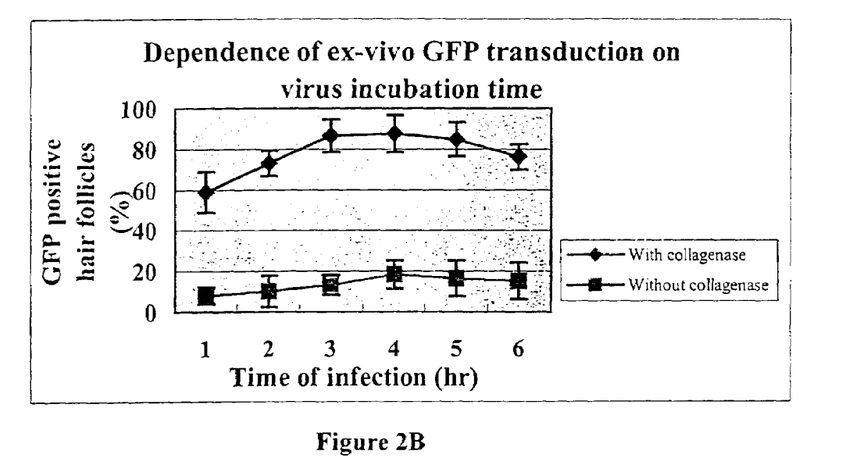

In additional similar experiments, both collagenase-treated and untreated histocultures were incubated with adenoviral GFP at $3.4 \times 10^8$ pfu/ml for 1 hr to 6 hr at 37° C. The number of GFP-positive hair follicles in collagenase-treated histocultures increased up to 80% with time of virus incubation for up to 4 hr. After 4 hr, no further increase was observed. In untreated histocultures, the number of GFP-positive hair follicles was very small and increased only slightly with time. These results are shown in FIG. 2B.

The number of GFP-positive hair follicles increased with the time of collagenase treatment of skin histocultures for up to 1 hr 30 min, after which the number decreased with time.

Figure 3A:
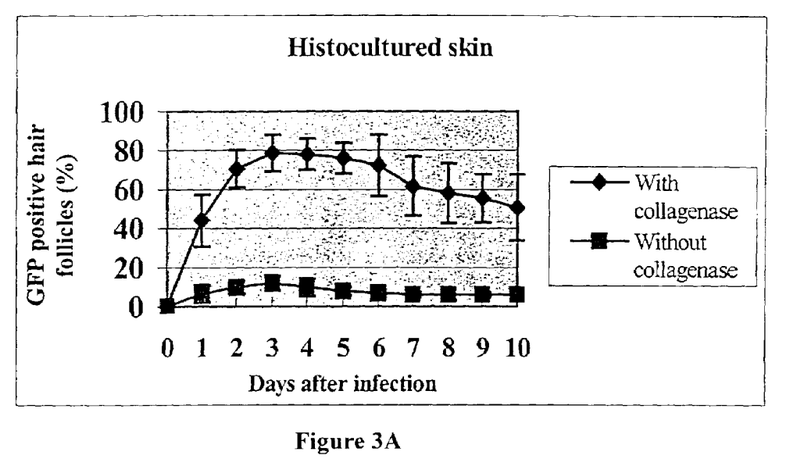
FIGS. 3A and 3B show the persistence of GFP in histoculture and grafted skin, respectively.

In these experiments, GFP was visualized in hair matrix cells of histocultured skin on day-1 after adenoviral-GFP treatment. On day-3 after adenoviral-GFP treatment, hair follicles were isolated from histocultured skin to determine the location of GFP fluorescence. GFP was extensively visualized in the majority of the cells in the hair bulbs and dermal papillae. On day-7 after adenoviral GFP treatment, GFP was visualized in hair shafts of histocultured skin. See FIG. 3A. GFP-positive and negative hair shafts and partially GFP-positive hair shafts were clearly distinguished by the specific GFP fluorescence, on day-3 after ex-vivo adenoviral-GFP gene treatment, GFP fluorescence was visualized in 79% of the hair follicles in collagenase-treated histocultured skin. In contrast, only 12% of hair follicles had GFP fluorescence in the untreated histocultured skin. See FIG. 3A. High GFP fluorescence was maintained in hair follicles for at least 35 days in histoculture.

In order to confirm the expression of the GFP gene in the hair follicles at different time points, RT-PCR analysis was used to detect GFP-specific mRNA in the adenoviral-GFP gene transduced histocultured skin at day-3, -6, -9, -12, -15, and -17. The RT-PCR products demonstrated that the GFP cDNA was specifically amplified from the total RNA at the above time points. Electrophoretic analysis demonstrated that amplified products from the adenoviral-GFP-transduced histocultured skin had the predicted size of 720 bp. RT-PCR with total RNA extracted from uninfected histocultured skin did not amplify this sequence.

TABLE 1

Expression of Adenovirus-delivered GFP in Hair Follicles of Histocultured Skin

| | With collagenase | | | Without collagenase | | |
|---|---|---|---|---|---|---|
| | Number of hair follicles | Number of GFP-positive hair follicles | Percent of GEP-positive hair follicles | Number of hair follicles | Number of GFP-positive hair follicles | Percent of GFP-positive hair follicles |
| Day 1 | 98 ± 3.46 | 57 ± 13.08 | 58.09 ± 12.9 | 51 ± 2.83 | 11 ± 2.83 | 21.98 ± 0.95 |
| Day 2 | 94 ± 15.1 | 61 ± 12.49 | 64.73 ± 5.07 | 58 ± 12.08 | 13 ± 1.41 | 22.84 ± 2.1 |
| Day 3 | 82 ± 3.46 | 55 ± 6.93 | 67.03 ± 7.28 | 58 ± 7.87 | 16 ± 1.41 | 28.16 ± 4.82 |

In all cases, visual observation showed that the hair follicles, hair bulbs, and dermal papilla of the histocultured skin showed expression of GFP.

Example 2

Transfer of Modified Histoculture to a Recipient

Eight-week-old female C57BL/10 mice whose hair follicles were in telogen phase were used as donors. The dorsal area was depilated with wax to induce anagen which occurred six days after depilation. Tissue was removed from the dorsal area and cut into small pieces, cultured, treated with collagenase, and infected with adenovirus containing GFP as described in Example 1. The skin pieces were then transplanted to the dorsal area of seven-week/three-day-old female nude mice. Observation of the grafted skin after transplant showed extensive expression of GFP in the hair follicles which expression was enhanced by the pretreatment with collagenase.

In more detail, to visualize the expression of the transgene in vivo, histocultured skin was grafted to nude mice or C57BL/10 mice after viral GFP transduction. Histocultured specimens were grafted within 24 hrs of harvest. Grafting surgery was performed in a laminar-flow hood using steirle procedures. Mice were anesthetized with Ketamine. 1×1 cm pieces of skin were grafted to a bed of similar size that was prepared by removing recipient mouse skin down to the fascia. Skin grafts were fixed in place with 6–0 nonabsorbable monofilament sutures.

Figure 3B:
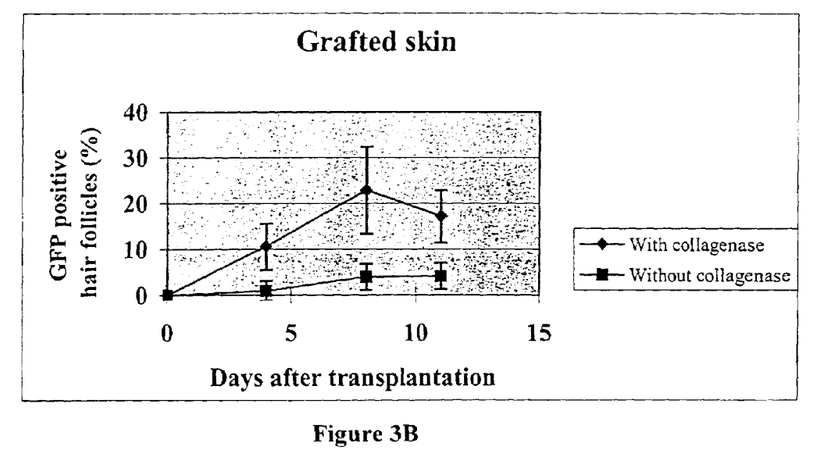

More extensive GFP fluorescence of hair follicles was visualized in the collagenase-treated histocultured skin after grafting than in untreated skin. On day-8 after grafting, GFP was visualized in 75% of hair follicles in the area of maximum fluorescence in the skin graft. After grafting, the percentage of hair follicles with GFP fluorescence in collagenase-treated skin was 5.7 times greater than in hair follicles of untreated skin. See FIG. 3B. GFP was visualized for similar time periods at similar efficiencies in GFP-adenoviral treated skin grafted to immune-competent C57BL10 mice as described above for skin grafted to immuno-deficient nude mice.

RT-PCR was performed at day-6, -8, and -10 on GFP-transduced grafted skin. GFP-specific mRNA was amplified at each point as well. These data confirm GFP gene expression for at least 17 days in histoculture and for at least 10 days after grafting of skin to mice.

Example 3

Cloning of the Streptomyces Tyrosinase Gene, the Upstream ORF-438 and the Internal Ribosome Entry Site (IRES)

The sequences encoding the *Streptomyces antibioticus* tyrosinase gene and ORF-438 were amplified by PCR from plasmid pIJ702 obtained from the American Type Culture Collection (ATCC #35287). Katz, E., et al,. *J. Gen. Microbiol.* (1983) 129:2703–2714.

Oligomers for PCR amplification were designed according to the sequence of *S. antibioticus* tyrosinase gene and ORF-438 cDNA. Bernan, V., et al., *Gene*, (1985) 37:101–110. In order to enhance expression of the bacterial gene in mammalian cells, the ORF-438 and tyrosinase-gene TGA termination codons were altered to TAA. The Kozak consensus sequence, GCCGCCACC, was added upstream, immediately preceding the ATG initiator codon in each case to facilitate translation efficiency.

The sequence of the ORF-438 upstream primer, which included the Kozak consensus sequence was 5'-CGGAATTCGCCGCCACCATGCCGGAACT-CACCCGTC-3' (SEQ ID NO:3). The downstream primer sequence was 5'-GGCTGATCATTAGTTGGAGGGGAAGGG-GAGGAGC-3' (SEQ ID NO4). The sequence of the tyrosinase upstream primer, which includes the Kozak consensus sequence was 5'-CTCGAGGCCGCCGCCATGACCGTCCG-CAAGAACCA-3' (SEQ ID NO:5). The downstream primer sequence was

5'-GGATCCTTAGACGTCGAAGGTGTAGTGC-3' (SEQ ID NO:6).

The PCR reaction conditions for both ORF-438 and tyrosinase were as follows: first denaturation at 97° C. for 10 min.; then 10 cycles of denaturation at 97° C. for 30 s; annealing at 66° C. for 30 s; and extension at 72° C. for 45 s; then a final extension at 72° C. for 10 min.

PCR oligomers were designed according to the sequence of the internal ribosome entry site (IRES) contained in the retroviral vector pLISN, obtained from Clonetech (Palo Alto, Calif.). The sequence of the upstream primer was 5'-GGCTGATCATTCGCCCTCTCCCTCCCC-3' (SEQ ID NO:7). The downstream primer sequence was

5'-AGCGGCCATTATCATCGTGTTTTTCAAAGG-3' (SEQ ID NO:8).

The IRES gene was amplified by PCR from pLXIN as the template. The PCR reaction conditions were as follows: first denaturation at 96° C. for 10 min; then 30 cycles of denaturation at 94° C. for 30 s; annealing at 50° C. for 30 s; and extension at 72° C. for 45 s; then a final extension at 72° C. for 10 min.

Electrophoretic analysis demonstrated that the amplified products had the predicted sizes of 438 bp, 800 bp and 580 bp for ORF-438, tyrosinase and IRES, respectively.

Example 4

Retroviral Vector pLme/SN Construction and Packaging

The construction of pLme/SN is described. Retroviral vector pLXSN (Clonetech, Palo Alto, Calif.) is a murine leukemia virus-based vector containing two promoters: the 5'-long terminal repeat (5'-LTR) to control the inserted genes and the SV40 promoter to control neomycin phosphotransferase (neoR). The 800-bp tyrosinase PCR product was digested by XhoI and inserted into the HapI/XhoI cloning site of pLXSN to obtain pLtyrSN. The ORF-438 and IRES PCR products were ligated at the Bcl I site and then inserted into the EcoRI/XhoI cloning site of pLtyrSN to obtain pLme/SN. Both the ORF-438 and tyrosinase genes are driven by the Moloney murine leukemia virus 5'-LTR in pLme/SN. The bicistronic sequence containing the ORF-438, IRES and tyrosinase genes under control of the 5'-LTR promoter is present in the vector.

pLmelSN was transfected into the PT67 packaging cell line using lipoTAXI (Clonetech, Palo Alto, Calif.; Stratagene, San Diego, Calif.). The transfected PT67 cell line was selected in DMEM medium containing 0.4 mg/ml G418 (Gibco BRL). The G418-resistant cells were cloned and expanded. After two weeks of selective culturing with G418, positive transfected cells, PT67-mel, were obtained.

Example 5

Expression in PT67-mel Cells

In order to confirm the expression of both the ORF-438 and the tyrosinase gene, RT-PCR analysis was used to detect their mRNA in the transfected packaging cells. The RT-PCR products demonstrated that the tyrosinase and ORF-438 genes from *S. antibioticus* were specifically amplified products from the total RNA of pLme/SN-transduced PT7-cells. As a control, mouse β-actin from both PT67-mel and PT67 cells was amplified by the RT-PCR. Electrophoretic analysis demonstrated that the amplified products from PT67-mel cells had the predicted sizes of 800 bp and 438 bp for tyrosinase and ORF-438, respectively. The RT-PCR reaction with total RNA from uninfected PT67 cells did not amplify these fragments.

In more detail, PT67-mel cells were digested with trypsin and pelleted by centrifugation. Total RNA was extracted by the guanidium thiocyanate method (MicroRNA Reagent Kit, Stratagene, San Diego, Calif.). RNA was quantified by measuring the absorbance at 260 nm. Approximately 10 μg of total RNA was reverse transcribed to first cDNA chains. Reverse transcription was carried out in 20 μl of first-strand buffer, 500 μM of each dNTP, and 20 units of AMV reverse transcriptase (Stratagene, San Diego, Calif.). The PCR primer for the first strand was pORF-438 antisense and pTyr antisense. Samples were incubated at 42° C. for 50 min. The products of the reverse transcription were amplified by the PCR reaction. Mouse β-actin was used as a standard to control the quality of the RNA (Stratagene, San Diego, Calif.).

Example 6

Tyrosinase Activity Assay

The transfected packaging cells were screened for the expression of active tyrosinase protein by measuring tyrosinase activity in the lysates of clones of G418-resistant packaging cells. Tyrosinase activity was assessed by the method described by Nakajima et al. *Pigment Cell Res* (1998) 11:12–17. The pLmelSN-infected PT67 packaging cells were plated at a density of 2,000 cells/well in 96 well plates. After 24 hours of culture, the packaging cells were washed with PBS and lysed with 1% Triton-100 (45 μl/well). After mixing the lysates by shaking, 5 μl of 10 mM L-DOPA were added to each well. Following incubation of the culture at 37° C. for 30 min., the absorbance was spectrophotometrically measured at 490 nm.

The DOPA-oxidase reaction was also used to detect melanin production in intact transfected PT67 cells. The cells were incubated with 1 mg/ml of DOPA and 2 mg/ml of tyrosine in PBS (pH 7.4) for 12 hr at 37° C. as previously described. See Kugelman, T. et al. *J. Invest Dermatol* (1961) 37:66–73.

Using the same conditions, cell supernatants were measured for melanin content at 490 nm. FIG. 3 shows PT67 clones 1–4 gentrate more melanin than control PT67. The tyrosinase-positive cells were identified by production of brown-colored melanin granules observed with brightfield microscopy. The brown pigment granules were observed only in pLme/SN-transfected cells.

Example 7

Culture of Albino-mouse Anagen Hair Follicles

Female albino mice C57BL/6J-Tyrosinase (c-2J), 8 week old, were purchased from the Jackson Laboratory. The growth phase of the hair cycle (anagen) was induced in the back skin, which had all follicles in the resting phase of the hair cycle (telogen). After general anesthesia, a warm wax/rosin mixture was applied and then peeled off the skin, depilating all telogen hair shafts and thereby inducing the follicles to enter anagen. See Schilli *J Invest Dermatol* (1998) 111:598–604.

On day-6 post-depilation, when all hair follicles were in anagen, back skins of the mice were collected after sacrifice. Small pieces of the mouse skin (2×5×2 mm) were cut with a scissors, and washed three times in HBSS. The harvested skin was incubated at 37° C. in MEM with antibiotics (100 μg gentamycin per ml, 10 μg ciprofroxacin per ml, 2.5 μg amphotericin-B per ml, 100 IU-100 μg penicillin-streptomycin per ml) for 30 min. (Sigma). The skins were washed three times with HBSS medium to remove residual antibiotics and put into collagen-containing gels for histoculture in Eagle's minimum essential medium (MEM) supplemented with 10% fetal bovine serum and gentamycin. Cultures were maintained at 37° C. in a gassed incubator with 5% $CO_2$.

Example 8

Infection of Cultured Albino-mouse Hair Follicles

The histocultured albino-mouse skin of Example 7 was co-cultured with PT67-mel cells as follows:

The PT67-mel cells from the highest producing clone were counted, seeded in 24-well plates, and grown at 37° C. until 80% confluence, and co-cultured with the histocultured albino skin in 24-well plates for 12, 24 and 72 hours. The histocultured skins were then mono-cultured in 24-well plates with fresh MEM medium and incubated for an additional 4–6 days. Small pieces of virus-infected skin were sampled at random. Fresh and frozen sections were prepared by standard techniques.

Melanin was observed in the hair matrix deep in the hair bulbs of the histocultures four days after retroviral infection. Melanin was also found in the upper part of the hair follicles and could be observed in both the hair matrix and hair shaft six days after infection.

In the initial experiments which involved co-culturing histocultured albino mouse skin with PT67-mel cells for 24 hours, approximately 2.5–15% of the skin histocultures contained melanin-producing hair follicles. No melanin was observed in histocultured albino-mouse skin not co-cultured with PT67-mel.

A time-course experiment was then carried out to determine if longer incubation times of the co-cultures of the albino skin and PT67-mel increased the efficiency of tyrosinase infection. The efficiency of infection of the histocultured skin was significantly increased with time of co-culture. After 12 hours co-culture, 7% (2 of 30 pieces) of skin produced melanin, and 15% of hair follicles (6 of 40) produced melanin. After 24 hours co-culture, 25% of skin pieces (5 of 20) produced melanin, as did 35% (28 of 80) of hair follicles. After 72 hours co-culture, 60% of skin pieces (12 of 20) produced melanin as did 53% (42 of 80) of hair follicles.

These results suggest that the virus titer and time exposure to virus can affect the transduction frequency.

The invention claimed is:

1. A method to introduce a nucleic acid molecule into a mammalian subject which method comprises
transplanting into the dermis of said subject at least one hair follicle that has been modified ex vivo to contain said nucleic acid molecule.

2. The method of claim 1 wherein said hair follicle has been modified ex vivo in a histoculture.

3. The method of claim 2 wherein said histoculture has been treated with collagenase prior to modifying said hair follicle.

4. The method of claim 1 wherein said hair follicle is in anagen.

5. The method of claim 1 wherein said follicle has been modified to contain said nucleic acid molecule by transducing with said nucleic acid or by lipofection.

6. The method of claim 1 wherein said follicle has been modified to contain said nucleic acid molecule by treating with a viral vector.

7. The method of claim 6 wherein said viral vector comprises the supernatant of a viral packaging cell, and/or wherein said viral vector comprises a retroviral vector, and/or wherein said viral vector comprises an adenoviral vector.

8. The method of claim 1 wherein said mammal is a mouse or a human.

9. A method to introduce a nucleic acid molecule into a mammalian subject which method comprises transplanting into a corresponding tissue of said mammal a histocultured intact tissue that has been modified ex vivo to contain said nucleic acid molecule;
wherein said histocultured intact tissue has been treated with collagenase prior to modifying said histocultured intact tissue with the nucleic acid.

10. The method of claim 9 wherein said modifying to contain said nucleic acid molecule comprises treating said histocultured intact tissue with a liposomal composition, or wherein said modifying to contain said nucleic acid molecule comprises transducing the cells of said histocultured intact tissue with said nucleic acid, or wherein said modifying to contain said nucleic acid molecule comprises treating said histocultured intact tissue with a viral vector.

11. The method of claim 9 wherein said histocultured intact tissue is dermis, or wherein said histocultured intact tissue is lymph tissue.

12. A method of delivering a nucleic acid to a hair follicle which method comprises maintaining said hair follicle in histoculture and treating said histoculture with a nucleic acid;
wherein said treating with a nucleic acid is preceded by the step of treating said histoculture with collagenase.

13. A method of delivering a nucleic acid to a an intact tissue which method comprises treating a histoculture of said intact tissue with said nucleic acid;
wherein said treating with a nucleic acid is preceded by the step of treating said histoculture with collagenase.

14. The method of claim 13 wherein said tissue is skin or lymphoid.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: GFP upstream primer

<400> SEQUENCE: 1
atggctagca aaggagaaga act                                   23

<210> SEQ ID NO 2
<211> LENGTH: 22
<212> TYPE: DNA
<213> ORGANISM: Artificial Sequence
<220> FEATURE:
<223> OTHER INFORMATION: GFP downstream primer

<400> SEQUENCE: 2
tcagttgtac agttcatcac tg                                    22

<210> SEQ ID NO 3
<211> LENGTH: 36
<212> TYPE: DNA
<213> ORGANISM: Artificial Sequence
<220> FEATURE:
<223> OTHER INFORMATION: ORF-438 upstream primer

<400> SEQUENCE: 3
cggaattcgc cgccaccatg ccggaactca cccgtc                     36

<210> SEQ ID NO 4
<211> LENGTH: 34
<212> TYPE: DNA
<213> ORGANISM: Artificial Sequence
<220> FEATURE:
<223> OTHER INFORMATION: ORF-438 downstream primer

<400> SEQUENCE: 4
ggctgatcat tagttggagg ggaaggggag gagc                       34

<210> SEQ ID NO 5
<211> LENGTH: 35
<212> TYPE: DNA
<213> ORGANISM: Artificial Sequence
<220> FEATURE:
<223> OTHER INFORMATION: Tyrosinase upstream primer

<400> SEQUENCE: 5
ctcgaggccg ccgccatgac cgtccgcaag aacca                      35

<210> SEQ ID NO 6
<211> LENGTH: 28
<212> TYPE: DNA
<213> ORGANISM: Artificial Sequence
<220> FEATURE:
<223> OTHER INFORMATION: Tyrosinase downstream primer

<400> SEQUENCE: 6
ggatccttag acgtcgaagg tgtagtgc                              28

```
<210> SEQ ID NO 7
<211> LENGTH: 28
<212> TYPE: DNA
<213> ORGANISM: Artificial Sequence
<220> FEATURE:
<223> OTHER INFORMATION: Upstream primer

<400> SEQUENCE: 7
ggctgatcat tcgccctct ccctcccc                                              28

<210> SEQ ID NO 8
<211> LENGTH: 30
<212> TYPE: DNA
<213> ORGANISM: Artificial Sequence
<220> FEATURE:
<223> OTHER INFORMATION: Downstream primer

<400> SEQUENCE: 8
agcggccatt atcatcgtgt ttttcaaagg                                           30
```